United States Patent [19]

Su

[11] Patent Number: 5,041,664

[45] Date of Patent: Aug. 20, 1991

[54] CONTINUOUS PROCESS FOR PREPARING QUATERNARY AMMONIUM SALTS

[75] Inventor: Wei-Yang Su, Austin, Tex.

[73] Assignee: Texaco Chemical Company, White Plains, N.Y.

[21] Appl. No.: 556,686

[22] Filed: Jul. 23, 1990

[51] Int. Cl.$^5$ .............................................. C07C 209/12
[52] U.S. Cl. ...................................... 564/296; 564/282
[58] Field of Search ................................ 584/282, 296

[56] References Cited

U.S. PATENT DOCUMENTS 3,175,008  3/1965  Shapiro et al. ....................... 564/296
3,311,659  3/1967  Birkelo et al. ....................... 564/282
3,360,563  12/1967  Bonta ................................... 564/282
3,758,586  9/1973  Coulson .............................. 564/282

Primary Examiner—James H. Reamer
Attorney, Agent, or Firm—Jack H. Park; Kenneth R. Priem; Cynthia L. Kendrick

[57] ABSTRACT

Disclosed is a process for the continuous preparation of quaternary ammonium chlorides from tertiary amines and organic chlorides wherein the catalyst comprises a metal oxide having Lewis acid sites, said oxide containing elements of Group IIA, IIIA, IIIB, IVA and IVB of the Periodic Table or a combination thereof.

6 Claims, No Drawings

CONTINUOUS PROCESS FOR PREPARING QUATERNARY AMMONIUM SALTS

BACKGROUND OF THE INVENTION

1. Field of the Invention

This invention relates to an improved process for preparing quaternary ammonium salts and more particularly this invention relates to a continuous process for preparing quaternary ammonium chlorides by reacting a tertiary amine with an organic chloride in the presence of a heterogeneous catalyst.

2. Related Art

The preparation of quaternary ammonium salts is known in the art. A good overview of the production of cationic surfactants from fatty nitriles is found in an article titled "Industrial Production of Fatty Amines and Their Derivatives",JAOCS, 61, No. 2(Feb. 1984). It is noted that the largest volume and most important class of quaternary ammonium salts is difattydimethyl ammonium salts, produced from secondary amines with methyl chloride under continuous addition of alkali.

In addition, known methods of preparation of quaternary ammonium compounds are discussed at p.526 in Encycl. Chem. Techn. 3rd Ed.(Hoechst) 19:521(1982). Generally a suitable tertiary amine is reacted with an alkylating agent, such as an alkyl ester. There are many variations in the final product because of the large number of diverse starting amines and alkylating agents. The tertiary amines used commercially are derived from synthetic or natural raw materials.

In U.S. Pat. No. 3,175,008 there is disclosed a method for preparing tetraaliphatic ammonium chloride by mixing an aliphatic secondary amine, sodium bicarbonate and alkyl alcohol having from 1 to 4 carbon atoms with methyl chloride at a temperature of at least 60°-70° C.

In U.S. Pat. No. 3,377,382 there are disclosed novel fatty quaternary ammonium compounds containing residual fatty acid monomers left after the polymerization of higher unsaturated fatty acids having about the same properties as dimethyl dihydrogenated tallow alkyl quaternaries which are commonly used for their softening properties.

In the processes discussed above the methods of production are not continuous. The discontinuous type reaction is less efficient because much more time is required to fill, heat and vent the reaction vessel. Also more of the alkyl chloride is lost as a result of repeated venting of the reaction vessel.

A continuous process for the manufacture of quaternary ammonium chlorides containing at least one aliphatic group of 8 to 22 carbons is disclosed in U S. Pat. No. 3,813,441 where amines are reacted with methyl chloride in the presence of an alkali metal hydroxide. In that invention the reaction is carried out in the presence of corresponding quaternary ammonium compounds which decreased saponification of methyl chloride. Further, the use of alkali hydroxides in place of sodium bicarbonate considerably improved the color of the quaternary ammonium compounds. The disadvantages of that process include corrosion caused by using caustic and also the need to dispose of a large amount of by-products.

It would be a distinct advance in the art if quaternary ammonium salts were continuously produced over a heterogeneous catalyst. If such a process offered high turnover rate, and high selectivity, such a process would fulfill a need in the art.

SUMMARY OF THE INVENTION

It is an object of the present invention to provide a method of preparing quaternary ammonium salts in a continuous process. More specifically, in accordance with the instant invention, there is provided a method for continuously reacting long chain tertiary amines with alkyl chlorides in the presence of a heterogeneous catalyst comprising a metal oxide with Lewis acid sites in the presence of a hindered alcohol solvent. In some cases water is used as a co-solvent.

DESCRIPTION OF THE PREFERRED EMBODIMENT

According to the present invention quaternary ammonium salts are produced in a continuous process using metal oxides with Lewis acid sites as catalysts. Quaternary ammonium salts were obtained by reacting tertiary amines which had at least one long aliphatic chain with organic chlorides according to the following equation:

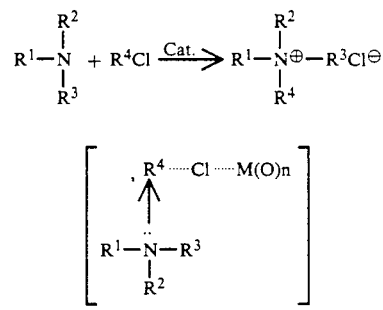

wherein $R^4$ is methyl or benzyl, $R^1$ represents an aliphatic radical having 8 to 22 carbon atoms, $R^2$ and $R^3$ represent an aliphatic radical of 1 to 22 carbon atoms.

The tertiary amines useful in this invention can be derived from synthetic or natural raw materials. The tertiary amines can generally be represented by the formula:

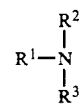

where $R^1$, $R^2$ and $R^3$ have the values defined above.

Suitable tertiary amines include the asymmetrical methyl difatty amines $R_2N(CH_3)$ and dimethyl fatty amines of the formula $RN(CH_3)_2$ and those derived from primary or secondary amines by reaction with ethylene oxide.

The amines should contain at least one aliphatic radical of 8-22 carbon atoms e.g. N,N-dimethyloctylamine, N,N-dimethyldecylamine, N,N-dimethylstearylamine, N,N-dimethyloleylamine, methyldioctylamine, methyldidecylamine and methyldistearylamine and especially amines having different lengths of chains of a statistical proportion as obtained by hydrogenation of fatty nitriles produced from fatty acids.

Useful amines include dihydrogenated tallowalkylmethylamine, dimethylcocoalkylamine, dicocoalkylmethylamine, didodecylmethylamine or tridodecylamine.

The organic chloride provides an alkylating agent. Suitable organic chlorides include methyl chloride, ethyl chloride, and benzyl chloride.

It has been surprisingly discovered in the instant invention that metal oxides with Lewis acid sites provide excellent catalysts for the continuous reaction to produce quaternary ammonium salts.

Compounds which may be employed as catalysts include, but are not limited to those containing elements of Group IIA, IIIA, IIIB, IVA and IVB of the Periodic Table. Suitable compounds include the oxides of aluminum, silicon, titanium, hafnium and zirconium or combinations thereof. Examples include alumina, silica(silicon dioxide), titania (titanium dioxide), hafnium dioxide and zirconia, as well as combinations thereof. Good results were observed using, for example, Norton catalyst carrier SZ5445, containing mainly silica, zirconia and hafnium dioxide. The catalyst may be in the form of powders, pellets, spheres and extrudates.

Commercially available catalysts which would fit this description for a metal oxide include Norton SZ5445 and Norton 64775. Norton SZ5445 is a 5-8 mesh catalyst incorporating $ZrO_2$-$SiO_2$-$HfO_2$. Norton 64775 is a titania catalyst carrier from Norton.

As solvents to be used for the quaternary ammonium compounds and for further diluting the reaction medium alcohols containing from 1 to 4 carbon atoms, preferably isopropanol, are suitable.

Where a solvent is employed an amount of from about 5 to 50% of the total content of the system is useful. About 20 to 30% is preferred.

The reaction preferably takes place in a stainless steel tubular upflow reactor. Atmospheric pressure is sufficient for the reaction to proceed. The reaction can occur at pressures of 0 psig to 3000 psig. Preferred pressures are in the range of 100 psig to 1500 psig. The temperature in the reactor should be between 50° C. and 150° C. and preferably about 70° C. to 130° C.

The mole ratio of amine to chloride can be from about 1:1.2 to 1.2:1, however a ratio of 1:1 is preferred.

The examples demonstrate not only the benefits of a continuous system, but the improved conversion of amines observed using the instant process. Example 1 demonstrates conversions of 99% or more which are obtained using the metal oxide catalyst in the continuous system.

The invention will be further illustrated by the following examples which are only for the purpose of illustration and are not to be regarded as limiting the invention in any way.

Examples

EXAMPLE 1

Preparation Of Dimethyl Dihydrogenated-tallowalkyl Ammonium Chloride

To a 550 cc DOWTHERM ® heated, stainless steel tubular upward flow reactor which had an inside diameter of 1.338" and a thermowell fabricated from ¼-inch O. D. tubing extended upward into the catalyst bed was charged 550 cc of Norton SZ5445 5-8 mesh catalyst carrier ($ZrO_2$-$SiO_2$-$HfO_2$ support). Dihydrogenatedtallowalkylmethylamine under the tradename KEMAMINE ® T-9701, sold by Witco Chemical, and methyl chloride/isopropanol solution were then run through the reactor bed at a total WHSV of 0.75 g/hr-cc and the reactant amine/chloride mole ratio of 1/1 with a 25% total isopropanol content. At 120° C. and 1000 psig, an off-white product was obtained and NMR spectrum analysis showed that about 99 to 100% of the amines were converted to the corresponding ammonium chloride.

EXAMPLE 2

Titania

The procedure of Example 1 was followed except that Norton titania carrier (Norton 64775) was used. An off-white product was obtained and NMR spectrum analysis showed that about 97% of amine conversion was obtained.

EXAMPLE 3

Alumina

The procedure of Example 1 was followed except that alumina was used. A yellow product was obtained and NMR spectrum analysis showed that about 95% amine conversion was obtained.

EXAMPLE 4

Pyrex Glass Beads

The procedure of Example 1 was followed except that Pyrex glass beads were used. An off-white product was obtained and NMR spectrum analysis showed that about 81% amine conversion was obtained. This is a comparative example which demonstrates that a catalyst with weaker Lewis acid sites has less catalytic effect.

EXAMPLE 5

The procedure of Example 1 was followed except the total WHSV was 1.10 g/hr-cc. An off-white product was obtained and NMR spectrum analysis showed that about 89% amine conversion was obtained.

EXAMPLE 6

Preparation Of Dimethylcocoalkylbenzylammonium Chloride

To a 550 cc DOWTHERM ® heated, stainless steel tubular, upward flow reactor was charged 550 cc of alumina catalyst carrier. Dimethylcocoalkylamine which was obtained from Ethyl Corp. under the tradename ADMA ® 1214 and benzyl chloride/isopropanol solution were then run through the reactor bed at a total WHSV of 0.87g/hr-cc and a reactant amine/chloride mole ratio of about 1:1 with a 25% total isopropanol content. At 120° C. and 1000 psig, a yellow product was obtained and NMR spectrum analysis showed that about all the amines were converted to the corresponding ammonium chloride.

EXAMPLE 7

The procedure of Example 6 was followed except that glass beads were used. A yellow product was obtained and NMR spectrum analysis showed that about all the amines were converted to the corresponding chloride quaternaries.

What is claimed is:

1. A continuous process for preparing quaternary ammonium salts which comprises reacting long chain tertiary amines having the formula

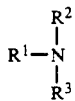

where $R^1$ represents an aliphatic radical having 8 to 22 carbon atoms and $R^2$ and $R^3$ represent an aliphatic radical of 1 to 22 carbon atoms with an alkyl chloride selected from the group consisting of methyl chloride, benzyl chloride and ethyl chloride, over a heterogeneous catalyst comprising an oxide of an element selected from Group IIA, IIIA, IIIB, IVA or IVB of the Periodic Table or a combination thereof in the presence of an alcohol solvent.

2. The process of claim 1 wherein the long chain tertiary amine is selected from the group consisting of dihydrogenatedtallowalkylmethylamine, dimethylcocoalkylamine and dicocoalkylmethylamine.

3. The process of claim 1 wherein the catalyst is selected from the group consisting of an oxide of silica, zirconia, titania, hafnium dioxide, alumina or a combination thereof.

4. The process of claim 1 wherein the solvent is isopropanol.

5. The process of claim 1 wherein the mole ratio of amine to chloride is from 1:1.2 to 1.2:1.

6. A continuous process for the preparation of dimethyl dihydrogenated tallow alkyl ammonium chloride which comprises reacting dihydrogenated tallow alkyl methyl amine with methyl chloride in the presence of isopropanol solvent over a catalyst comprising a combination of an oxide of zirconium, hafnium dioxide and silicon.

* * * * *